United States Patent [19]
Rivier et al.

[11] Patent Number: 4,652,550
[45] Date of Patent: Mar. 24, 1987

[54] GNRH ANTAGONISTS VII

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 653,867

[22] Filed: Sep. 21, 1984

Related U.S. Application Data

[63] Continuation-in-part of Ser. No. 612,072, May 21, 1984, Pat. No. 4,569,927.

[51] Int. Cl.$^4$ .................... A61K 37/43; C07K 7/20
[52] U.S. Cl. .................................. 514/15; 530/313; 514/800
[58] Field of Search ............... 260/112.5 LH; 514/15, 514/800; 530/313

[56] References Cited

U.S. PATENT DOCUMENTS

| 4,234,571 | 11/1980 | Nestor et al. | 260/112.5 LH |
|---|---|---|---|
| 4,317,815 | 3/1982 | Coy et al. | 260/112.5 LH |
| 4,341,767 | 7/1982 | Nestor et al. | 260/112.5 LH |
| 4,444,759 | 4/1984 | Rivier et al. | 260/112.5 LH |
| 4,481,190 | 11/1984 | Nestor et al. | 260/112.5 LH |

OTHER PUBLICATIONS

Coy et al., *Endocrinology*, vol. 110, No. 4, 1982, pp. 1445-1447.
Yalie et al., *Chem. Pharm. Bull.*, vol. 27, No. 8, 1979, pp. 1907-1911.

Primary Examiner—Delbert R. Phillips
Attorney, Agent, or Firm—Fitch, Even, Tabin & Flannery

[57] ABSTRACT

Peptides which inhibit the secretion of gonadotropins by the pituitary gland and inhibit the release of steroids by the gonads. Administration of an effective amount prevents ovulation of female mammalian eggs and/or the release of steroids by the gonads. The peptides have the structure: $X-R_1-R_2-R_3-Ser-Tyr-R_6-R_7-Arg-Pro-R_{10}$ wherein X is hydrogen or an acyl group having 7 or less carbon atoms; $R_1$ is dehydro-Pro or $\beta$-D-NAL; $R_2$ is Cl-D-Phe, F-D-Phe, $NO_2$-D-Phe, $C^\alpha$Me-4-Cl-D-Phe, $Cl_2$-D-Phe or Br-D-Phe; $R_3$ is D-Trp, substituted D-Trp, $\beta$-D-NAL, or D-PAL; $R_6$ is a D-isomer of a lipophilic amino acid or is 4-$NH_2$-D-Phe, D-Lys, D-Orn, D-Har, D-His, 4-gua-D-Phe, D-PAL or D-Arg; $R_7$ is Nle, Phe, Met, Tyr, Nva, Trp, Cys, PAL or 4F-D-Phe; and $R_{10}$ is Gly-$NH_2$ or D-Ala-$NH_2$; provided however that when $R_1$ is $\beta$-D-NAL, then $R_6$ is 4-$NH_2$-D-Phe, D-Lys, D-Orn, D-Har, D-His, 4-gua-D-Phe, D-PAL or D-Arg.

21 Claims, No Drawings

GNRH ANTAGONISTS VII

This invention was made with Government support under Contract No. NO1-HD-0-2836 and/or Grant No. HD 13527 awarded by the National Institutes of Health. The Government has certain rights in this invention.

This application is a continuation-in-part of our Ser. No. 612,072, filed May 21, 1984, now U.S. Pat. No. 4,569,927.

The present invention relates to peptides which inhibit the release of gonadotropins by the pituitary gland in mammalians, including humans, and to methods of preventing ovulation and/or inhibiting the release of steroids. More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure:

p-Glu-His-Trp-Ser-Tyr-Gly-Leu-Arg-Pro-Gly-NH₂

Peptides are compounds which contain two or more amino acids in which the carboxyl group of one acid is linked to the amino group of the other acid. The formula for GnRH, as represented above, is in accordance with conventional representation of peptides where the amino terminus appears to the left and the carboxyl terminus to the right. The position of the amino acid residue is identified by numbering the amino acid residues from left to right. In the case of GnRH, the hydroxyl portion of the carboxyl group of glycine has been replaced with an amino group (NH₂). The abbreviations for the individual amino acid residues above are conventional and are based on the trivial name of the amino acid, e.g. p-Glu is pyroglutamic acid, His is histidine, Trp is tryptophan, Ser is serine, Tyr is tyrosine, Gly is glycine, Leu is leucine, Orn is ornithine, Arg is arginine, Pro is proline, Sar is sarcosine, Phe is phenylalanine and Ala is alanine. These amino acids together with valine, isoleucine, threonine, lysine, aspartic acid, asparagine, glutamine, cysteine, methionine, phenylalanine, and proline are generally considered to be the common, naturally occurring or protein-derived amino acids. Except for glycine, amino acids of the peptides of the invention are of the L-configuration unless noted otherwise.

It is well known that the substitution of D-amino acids for Gly in the 6-position of the GnRH decapeptide or nonapeptide provides GnRH analogs having from substantially greater potency than GnRH to effect the release of LH and FSH (i.e. the gonadotropins) by the pituitary gland of mammalians. It is also known that substitution of various amino acids for His (or the deletion of His) at the 2-position of the GnRH decapeptide produces analogs having an inhibitory effect on the release of LH and other gonadotropins by the pituitary gland of mammalians.

There are reasons for desiring to prevent ovulation in female mammalians, and the administration of GnRH analogs that are antagonistic to the normal function of GnRH have been used to suppress or delay ovulation. For this reason, analogs of GnRH which are antagonistic to GnRH are being investigated for their potential use as a contraceptive or for regulating conception periods. GnRH antagonists may also be used for the treatment of precocious puberty and endometriosis. Such antagonists have also been found useful to regulate the secretion of gonadotropins in male mammals and can be employed to arrest spermatogenesis, e.g. as male contraceptives, and for treatment of prostatic hypertrophy. It is desired to provide improved peptides which are strongly antagonistic to endogenous GnRH and which prevent secretion of LH and the release of steroids by the gonads of mammals.

SUMMARY OF THE INVENTION

The present invention provides peptides which inhibit the release of gonadotropins in mammalians, including humans, and it also provides methods for inhibiting the release of steroids by the gonads of male and female mammalians. The improved GnRH analogs are strongly antagonistic to GnRH and have an inhibitory effect on the reproduction processes of mammalians. These analogs may be used to inhibit the production of gonadotropins and sex hormones under various circumstances including precocious puberty, hormone dependent neoplasia, dysmenorrhea and endometriosis.

Generally, in accordance with the present invention, peptides have been synthesized which strongly inhibit the secretion of gonadotropins by the pituitary gland of mammalians, including humans, and/or inhibit the release of steroids by the gonads. These peptides are analogs of GnRH wherein there is a 1-position substitution, preferably dehydro-Pro or β-(1- or 2-naphthyl)-D-alanine (hereinafter β-D-1NAL or β-D-2NAL), a 2-position substitution in the form of a halogenated D-Phe, a 3-position substitution in the form of D-Trp, substituted D-Trp, β-D-NAL or D-PAL, a 6-position substitution and a substitution in the 7-position selected from Nle, Phe, Nva, Met, Tyr, Trp, Cys, PAL and 4F-D-Phe. The 1-position substituent may be modified so that its alpha amino group contains an acyl group, such as formyl(Fr), acetyl, acrylyl, vinylacetyl(Vac) or benzoyl(Bz), with acetyl(Ac) and acrylyl(Acr) being preferred. PAL and D-PAL represent the L- and D-isomers of pyridyl-alanine where the β-carbon of Ala is linked to the 3-position on the pyridine ring. When β-D-NAL is present in the 1-position, a hydrophilic D-amino acid residue, such as 4-NH₂-D-Phe, 4-guanidino-D-Phe, D-His, D-Lys, D-Orn, D-Arg, D-Har(Homoarginine) or D-PAL is present in the 6-position. When dehydro-Pro is present in the 1-position, a D-isomer of a lipophilic amino acid, such as D-Trp, D-Phe, D-Leu, D-Ile, D-Nle, D-Tyr, D-Val, D-Ala, D-Ser(OtBu), β-D-2NAL or (imBzl)D-His is preferably in the 6-position, but D-PAL may be used. A substitution in the 10-position of D-Ala for Gly is considered optional, along with other substitutions mentioned hereinafter.

Because these peptides are highly potent to inhibit release of LH, they are often referred to as GnRH antagonists. The peptides inhibit ovulation of female mammals when administered at very low levels at proestrus and are also effective to cause resorption of fertilized eggs if administered shortly after conception. These peptides are also effective for the contraceptive treatment of male mammals.

DETAILED DESCRIPTION OF THE PREFERRED EMBODIMENTS

More specifically, the peptides of the present invention are represented by the following Formula I:

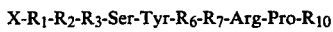

wherein X is hydrogen or an acyl group having 7 or less carbon atoms; $R_1$ is dehydro-Pro or $\beta$-D-NAL; $R_2$ is Cl-D-Phe, F-D-Phe, $NO_2$-D-Phe, $C^\alpha$Me-4-Cl-D-Phe, $Cl_2$-D-Phe or Br-D-Phe; $R_3$ is (Y) D-Trp, $\beta$-D-NAL, or D-PAL with Y being H, $NO_2$, $NH_2$, $OCH_3$, F, Cl, Br, $CH_3$, $N^{in}$For or $N^{in}$Ac; $R_6$ is a D-isomer of a lipophilic amino acid or is 4-$NH_2$-D-Phe, D-Lys, D-Orn, D-Har, D-His, 4-gua-D-Phe, D-PAL or D-Arg; $R_7$ is Nle, Phe, Met, Nva, Tyr, Trp, Cys, PAL or 4-F-D-Phe; and $R_{10}$ is Gly-$NH_2$ or D-Ala-$NH_2$; provided however that when $R_1$ is $\beta$-D-NAL, then $R_6$ is 4-$NH_2$-D-Phe, D-Lys, D-Orn, D-Har, D-His, 4-gua-D-Phe, D-PAL or D-Arg.

By $\beta$-D-NAL is meant the D-isomer of alanine which is substituted by naphthyl on the $\beta$-carbon atom, i.e., also 3-D-NAL. Preferably $\beta$-D-2NAL is employed, the attachment to naphthalene is at the 2-position on the ring structure; however, $\beta$-D-1NAL may also be used. PAL represents alanine which is substituted by pyridyl on the $\beta$-carbon atom; preferably the linkage is to the 3-position on the pyridine ring. In D-Trp in the 3-position, single substitutions for hydrogen are made in either the 5- or 6-position, which are selected from chloro, fluoro, bromo, methyl, amino, methoxy and nitro, with chloro, fluoro and nitro being preferred. Alternatively, the indole nitrogen may be acylated, e.g. with formyl ($N^{in}$For- or 1For-) or with acetyl. $N^{in}$For-D-Trp and 6$NO_2$-D-Trp are the preferred substituted residues. By ($C^\alpha$Me-4Cl) Phe is meant a phenylalanine residue that is substituted with chlorine in the para-position and the alpha-carbon atom of which is methylated.

The peptides of the present invention can be synthesized by classical solution synthesis or by a solid phase technique using a chloromethylated resin, a methylbenzhydrylamine resin (MBHA), a benzhydrylamine (BHA) resin or any other suitable resin known in the art. The solid phase synthesis is conducted in a manner to stepwise add the amino acids in the chain in the manner set forth in detail in the U.S. Pat. No. 4,211,693. Side-chain protecting groups, as are well known in the art, are preferably added to Ser, Tyr and Arg when present, as well as to certain of the substituents, and may optionally be added to Trp, before these amino acids are coupled to the chain being built upon the resin. Such a method provides the fully protected intermediate peptidoresin.

The intermediates of the invention may be represented:

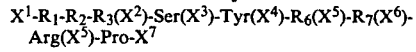

wherein: $X^1$ is an $\alpha$-amino protecting group of the type known to be useful in the art in the stepwise synthesis of polypeptides and when X in the desired peptide composition is a particular acyl group, that group may be used as the protecting group. Among the classes of $\alpha$-amino protecting groups covered by $X^1$ are (1) acyl-type protecting groups, such as formyl(For), trifluoroacetyl, phthalyl, p-toluenesulfonyl(Tos), benzoyl(Bz), benzenesulfonyl, o-nitrophenylsulfenyl(Nps), tritylsulfenyl, o-nitrophenoxyacetyl, acrylyl(Acr), chloroacetyl, acetyl-(Ac) and $\gamma$-chlorobutyryl; (2) aromatic urethan-type protecting groups, e.g., benzyloxycarbonyl (Z) and substituted benzyloxycarbonyl, such as p-chloro-benzyloxycarbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred $\alpha$-amino protecting group is Boc when X is hydrogen.

$X^2$ is hydrogen or a protecting group for the indole nitrogen, such as benzyl; however in many syntheses there is no need to protect Trp.

$X^3$ is hydrogen or a protecting group for the alcoholic hydroxyl group of Ser, such as one selected from the group consisting of acetyl, benzoyl, tetrahydropyranyl, tert-butyl, trityl, benzyl and 2,6-dichlorobenzyl, with benzyl being preferred. Alternatively, when a substitution is made for Ser, $X^3$ may be a protecting group for a side chain amino group, such as Tos, Z or ClZ.

$X^4$ is hydrogen or a protecting group for the phenolic hydroxyl group of Tyr, if Tyr is present, selected from the group consisting of tetrahydropyranyl, tert-butyl, trityl, benzyl, Z, 4-bromobenzyloxycarbonyl and 2,6-dichlorobenzyl. 2,6-dichlorobenzyl (DCB) is preferred.

$X^5$ is a protecting group for the side chain guanidino group or the amino group or the imidazole group of Arg, Lys, His or the like, such as nitro, Tos, trityl, benzyloxycarbonyl, adamantyloxycarbonyl, Z, and Boc or a protecting group for Trp as $X^2$, or $X^5$ may be hydrogen, which means there is no protection on the side chain group atoms. Tos is generally preferred.

$X^6$ is hydrogen, a protecting group for Tyr, such as $X^4$ or a protecting group for Cys preferably selected from the class consisting of p-methoxybenzyl(MeOBzl), p-methylbenzyl, acetamidomethyl, trityl and Bzl. The most preferred protecting group is p-methoxybenzyl.

$X^7$ may be Gly-O-$CH_2$-[resin support]; D-Ala-O-$CH_2$-[resin support]; Gly-NH-[resin support] or D-Ala-NH-[resin support]; and it may be OH, ester, amide or hydrazide either of Gly or D-Ala.

The criterion for selecting side chain protecting groups for $X^2$–$X^6$ is that the protecting group should be stable to the reagent under the reaction conditions selected for removing the $\alpha$-amino protecting group at each step of the synthesis. The protecting group should not be split off under coupling conditions, and the protecting group should be removable upon completion of the synthesis of the desired amino acid sequence under reaction conditions that will not alter the peptide chain.

When the $X^7$ group is Gly-O-CH$_2$-[resin support] or D-Ala-O-CH$_2$-[resin support], the ester moiety of one of the many functional groups of the polystyrene resin support is being represented. When the $X^7$ group is Gly-NH-[resin support] or D-Ala-NH-[resin support], an amide bond connects Gly or D-Ala to BHA resin or to a MBHA resin.

When X is acetyl, for example, in the final formula, it may be possible to employ it as the $X^1$ protecting group for the α-amino group of D-NAL or whatever amino acid is used in the 1-position by adding it before the coupling of this last amino acid to the peptide chain. However, a reaction is preferably carried out with the peptide on the resin (after deblocking the α-amino group while the side-chain groups remain protected), e.g. by reacting with acetic acid in the presence of dicyclohexyl carbodiimide (DCC) or preferably with acetic anhydride or by another suitable reaction as known in the art.

The fully protected peptide can be cleaved from a chloromethylated resin support by ammonolysis, as is well known in the art, to yield the fully protected amide intermediate. Deprotection of the peptide, as well as cleavage of the peptide from a benzhydrylamine resin, can take place at 0° C. with hydrofluoric acid (HF). Anisole is preferably added to the peptide prior to treatment with HF. After the removal of HF, under vacuum, the cleaved, deprotected peptide is conveniently treated with ether, decanted, taken-up in dilute acetic acid and lyophilized.

Thus the invention also provides a method for making a peptide or a nontoxic salt thereof, said peptide having the formula:

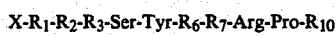

X-R$_1$-R$_2$-R$_3$-Ser-Tyr-R$_6$-R$_7$-Arg-Pro-R$_{10}$ wherein X is hydrogen or an acyl group having 7 or less carbon atoms; R$_1$ is dehydro-Pro or β-D-NAL; R$_2$ is Cl-Phe, F-D-Phe, NO$_2$-D-Phe, C$^\alpha$Me-4-Cl-D-Phe, Cl$_2$-D-Phe or Br-D-Phe; R$_3$ is D-Trp, substituted D-Trp, β-D-NAL, or D-PAL; R$_6$ is a D-isomer of a lipophilic amino acid or is 4-NH$_2$-D-Phe, D-Lys, D-Orn, D-Har, D-His, 4-gua-D-Phe, D-PAL or D-Arg; R$_7$ is Nle, Phe, Met, Tyr, Nva, Trp, Cys, PAL or 4-F-D-Phe; and R$_{10}$ is Gly-NH$_2$ or D-Ala-NH$_2$; provided however that when R$_1$ is β-D-NAL, then R$_6$ is 4-NH$_2$-D-Phe, D-Lys, D-Orn, D-Har, D-His, 4-gua-D-Phe, D-PAL or D-Arg; which method comprises (a) forming an intermediate compound having the formula:

X$^1$-R$_1$-R$_2$-R$_3$(X$^2$)-Ser(X$^3$)-Tyr(X$^4$)-R$_6$(X$^5$)-R$_7$(X$^6$)-Arg(X$^5$)-Pro-X$^7$, wherein $X^1$ is hydrogen or an α-amino protecting group; $X^2$ is hydrogen or a protecting group for the indole nitrogen; $X^3$ is hydrogen or a protecting group for the alcoholic hydroxyl group of Ser or for a side-chain amino group; $X^4$ is hydrogen or a protecting group for the phenolic hydroxyl group of Tyr; $X^5$ and $X^6$ are each either hydrogen or a protecting group for the respective side chain that is present; and $X^7$ is selected from the group consisting of Gly-O-CH$_2$-(resin support), D-Ala-O-CH$_2$-(resin support), Gly-NH-(resin support), D-Ala-NH-(resin support), Gly-NH$_2$, and esters, amides and hydrazides; (b) splitting off one or more of the groups $X^1$ to $X^6$ and/or cleaving from any resin support included in $X^7$ and, if desired, (c) converting a resulting peptide into a nontoxic salt thereof.

Purification of the peptide is effected by ion exchange chromotography on a CMC column, followed by partition chromotography using the elution system: n-butanol; 0.1N acetic acid (1:1 volume ratio) on a column packed with Sephadex G-25, or by using HPLC, as known in the art, or more specifically as set forth in J. Rivier, et al. *J. Chromatography*, 288 (1984) 303–328, the text of which is incorporated herein by reference.

The peptides of the invention are effective at levels of less than 100 micrograms per kilogram of body weight, when administered at about noon on the day of proestrus to prevent ovulation in female rats. For prolonged suppression of ovulation, it may be necessary to use dosage levels in the range of from about 0.1 to about 2.5 milligrams per kilogram of body weight. These antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

EXAMPLE I

Peptides as indicated in TABLE I having the formula:

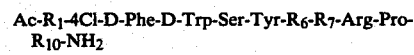

Ac-R$_1$-4Cl-D-Phe-D-Trp-Ser-Tyr-R$_6$-R$_7$-Arg-Pro-R$_{10}$-NH$_2$ are prepared by the solid-phase procedure referred to above.

TABLE I

| | R$_1$ | R$_6$ | R$_7$ | R$_{10}$ |
|---|---|---|---|---|
| 1 | β-D-2NAL | D-Arg | Nle | D-Ala |
| 2 | " | " | Met | " |
| 3 | " | " | Tyr | " |
| 4 | " | " | Nle | Gly |
| 5 | " | " | Met | " |
| 6 | " | " | Tyr | " |
| 7 | " | " | Phe | D-Ala |
| 8 | " | " | 4F—D-Phe | " |
| 9 | " | " | Cys | " |
| 10 | dehydro Pro | D-Trp | Nle | " |
| 11 | β-D-2NAL | D-Arg | Trp | " |
| 12 | " | D-Har | Cys | " |
| 13 | " | D-Lys | Nva | " |
| 14 | " | D-Arg | PAL | " |
| 15 | dehydro Pro | D-Leu | Tyr | NHCH$_2$CH$_3$ |

For purposes of an example, a representative solid phase synthesis of Peptide No. 1 above, which is referred to as [Ac-β-D-2NAL$^1$, 4Cl-D-Phe$^2$, D-Trp$^3$, D-Arg$^6$, Nle$^7$, D-Ala$^{10}$]-GnRH is set forth hereinafter. This peptide has the following formula:

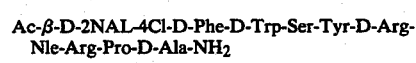

Ac-β-D-2NAL-4Cl-D-Phe-D-Trp-Ser-Tyr-D-Arg-Nle-Arg-Pro-D-Ala-NH$_2$

A BHA resin is used, and Boc-protected D-Ala is coupled to the resin over a 2-hour period in CH$_2$Cl$_2$ using a 3-fold excess of Boc derivative and DCC as an activating reagent. The D-Ala residue attaches to the BHA resin by an amide bond.

Following the coupling of each amino acid, washing, deblocking and coupling of the next protected amino acid is carried out in accordance with the following schedule using an automated machine and beginning with about 5 grams of resin:

| STEP | REAGENTS AND OPERATIONS | MIX TIMES MIN. |
|---|---|---|
| 1 | CH$_2$Cl$_2$ wash-80 ml. (2 times) | 3 |
| 2 | Methanol (MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$-70 ml. (2 times) | 10 |
| 5 | Isopropyl alcohol + 1% ethanedithiol wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30-300 |
| 10 | MeOH wash-40 ml. (2 times) | 3 |
| 11 | TEA 12.5 percent in CH$_2$Cl$_2$-70 ml. (1 time) | 3 |
| 12 | MeOH wash-30 ml. (2 times) | 3 |
| 13 | CH$_2$Cl$_2$ wash-80 ml. (2 times) | 3 |

If the coupling should be carried out manually, after step 13, an aliquot may be taken for a ninhydrin test: if the test is negative, one proceeds to step 1 for coupling of the next amino acid; if the test is positive or slightly positive, one repeats steps 9 through 13.

The above schedule is used for coupling of each of the amino acids of the peptide of the invention after the first amino acid has been attached. N$^\alpha$Boc protection is used for each of the remaining amino acids throughout the synthesis. N$^\alpha$-Boc-$\beta$-D-2NAL is prepared by a method known in the art, e.g. as described in detail in U.S. Pat. No. 4,234,571, issued Nov. 18, 1980. The side chain of Arg is protected with Tos. OBzl is used as a side chain protecting group for the hydroxyl group of Ser, and DCB is used to protect the phenolic hydroxyl of Tyr. D-Trp is left unprotected. N$^\alpha$Boc-$\alpha$-D-2NAL is introduced as the final amino acid. Boc-Arg(Tos) and Boc-D-Trp, which have low solubility in CH$_2$Cl$_2$, are coupled using DMF:CH$_2$Cl$_2$ mixtures.

After deblocking the $\alpha$-amino group at the N-terminus, acetylation is achieved using a large excess of acetic anhydride in dichloromethane. This produces the following molecule: Ac-$\beta$-DNAL-4Cl-D-Phe-D-Trp-Ser(OBzl)-Tyr(DCB)-D-Arg(Tos)-Nle-Arg(Tos)-Pro-D-Ala-NH-[resin support]. The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3M NH$_4$OAc in 50/50 methanol/water) followed by partition chromatography in a gel filtration column using the elution system: n-Butanol; 0.1N Acetic acid (1:1—volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter as $[\alpha]_D^{22} = -28.0° \pm 1 (c=1, 50\%$ acetic acid).

The peptide is assayed in vitro and in vivo. The in vitro test is made using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i.e. [Ac-dehydro Pro$^1$, 4-F-D-Phe$^2$, D-Trp$^{3,6}$]-GnRH or the test peptide, in concentrations ranging from 0.01 to 10 nanomolar. The amount of LH secreted in the samples treated only with GnRH is compared with that secreted by the samples treated with the peptide plus GnRH.

The ability of the test peptide to reduce the amount of LH released by 3 nanomolar GnRH is compared to that of the present standard peptide. The results are calculated using 3-5 doses of each of the peptides by the statistical program BIOPROG (provided by D. Rodbard NICHD) and are expressed as a potency relative to the present standard. The standard peptide usually blocks 50% of the LH released by GnRH at less than a ratio of $$\frac{0.1 \text{ [antagonist]}}{1 \text{ [GnRH]}}$$

Peptide No. 1 demonstrates equal effectiveness at a level of about 63% of the level of the present standard.

The peptide described hereinabove is also used to determine effectiveness to prevent ovulation in female rats. In this test, a specified number of mature female Sprague-Dawley rats, each having a body weight from 225 to 250 grams, is injected with 10 micrograms of peptide in corn oil at about noon on the day of proestrus. Proestrus is the afternoon before estrus (ovulation). A separate female rat group is used as a control to which the peptide is not administered. Each of the control female rats has ovulation at estrus; of the rats treated, none of them ovulates. As a result, the peptide is considered to be significantly effective to prevent ovulation of female rats at a very low dosage, and the peptide is considered to be totally effective at a dose of about ten micrograms. Additional testing is carried out at lower dosages with the results being set forth in TABLE IA hereinafter.

Peptides Nos. 2-15 are similarly synthesized and purified. After amino acid analysis is completed, the purity is confirmed by HPLC using different solvent systems. In vitro testing in similar fashion shows the peptides each to have a biological potency to inhibit the secretion of LH and FSH. In vivo testing is carried out at varying dosages for various of the peptides, and the results are shown in TABLE IA.

TABLE IA

| Peptide No. | $[\alpha]_D^{22}$ | Dose (μg) | in vivo No. Ovulating |
|---|---|---|---|
| 1. | −28.0 | 1 | 3/16 |
|  |  | 0.5 | 9/10 |

TABLE IA-continued

| Peptide No. | $[\alpha]_D^{22}$ | Dose (μg) | in vivo No. Ovulating |
|---|---|---|---|
| 2. | −22.4 | 2.5 | 2/15 |
|  |  | 1 | 3/9 |
| 3. | −18.8 | 1 | 0/10 |
|  |  | 0.5 | 4/7 |
| 7. | −22.5 | 2.5 | 0/8 |
|  |  | 1 | 6/15 |
|  |  | 0.5 | 2/3 |
| 8. | −23.8 | 2.5 | 0/10 |
|  |  | 1 | 4/7 |
| 9. | −22.0 | 5 | 6/8 |
| 11. | −17.2 | 2.5 | 0/8 |
|  |  | 1.0 | 6/6 |

All peptides listed in Table I are considered effective to block GnRH-induced LH secretion in vitro at some reasonable concentration. Many of these peptides are much more potent in vivo than the present standard.

All of the peptides are considered to be effective to prevent ovulation of female mammals at very low dosages, and some selected ones are considered to be at least as potent as any GnRH antagonists previously known and tested.

EXAMPLE II

Peptides as indicated in TABLE II having the formula: Ac-R$_1$-(W)D-Phe-R$_3$-Ser-Tyr-R$_6$-R$_7$-Arg-Pro-D-Ala-NH$_2$ are prepared by the solid-phase procedure referred to above.

TABLE II

|  | R$_1$ | W | R$_3$ | R$_6$ | R$_7$ |
|---|---|---|---|---|---|
| 16 | β-D-2NAL | 4Br | (6NO$_2$)D-Trp | D-Arg | Nle |
| 17 | " | 4F | " | D-His | Tyr |
| 18 | " | " | D-Trp | 4gua-D-Phe | " |
| 19 | dehydro Pro | " | " | D-Trp | Phe |
| 20 | " | 4NO$_2$ | β-D-1NAL | D-Val | Met |
| 21 | β-D-2NAL | 4Cl | N$^{in}$For-D-Trp | D-Arg | Nle |
| 22 | " | " | " | " | Nva |
| 23 | dehydro Pro | 4Br | β-D-2NAL | D-Tyr | 4F—D-Phe |
| 24 | " | " | " | D-Nle | Trp |
| 25 | " | C$^\alpha$Me—4Cl | " | D-Phe | Nle |
| 26 | " | " | D-PAL | β-D-2NAL | Phe |
| 27 | " | 4Cl | " | " | Leu |
| 28 | β-D-2NAL | 4NO$_2$ | " | D-Orn | 4F—D-Phe |
| 29 | " | " | " | 4NH$_2$—D-Phe | Met |
| 30 | " | 3,4Cl | D-Trp | " | Tyr |
| 31 | " | 4Cl | D-PAL | D-PAL | Leu |

In vitro and/or in vivo testing of the peptides specified in Table II shows that the peptides listed in Table II are considered effective to block GnRH-induced LH secretion in vitro at a reasonable concentration. Many of these peptides are more potent in vivo than the present standard. All of the peptides are considered to be effective to prevent ovulation of female mammals at very low dosages.

EXAMPLE III

Peptides as indicated in TABLE III having the formula: X-β-D-2NAL-4F-D-Phe-D-Trp-Ser-Tyr-R$_6$-R$_7$-Arg-Pro-D-Ala-NH$_2$ are prepared by the solid-phase procedure referred to above.

TABLE III

|  | X | R$_1$ | R$_6$ | R$_7$ |
|---|---|---|---|---|
| 32 | Acr | dehydro-Pro | D-Trp | Tyr |
| 33 | " | " | D-Ile | PAL |
| 34 | " | " | D-Val | Nle(3F—Phe$^5$) |
| 35 | " | Pro | D-Ser(OtBu) | Phe |
| 36 | H | D-Phe | (imBzl)D-His | Cys(Orn$^4$) |
| 37 | Bz | " | D-Trp | Met |
| 38 | " | D-pGlu | D-Trp | Nle(3I-Tyr$^5$) |
| 39 | Fr | β-D-1NAL | D-Arg | Phe(acetate salt) |
| 40 | " | " | D-Har | Tyr(aBu$^4$) |
| 41 | Vac | β-D-2NAL | D-Lys | Nva(acetate salt) |
| 42 | " | D-Phe | D-Nle | Cys |
| 43 | H | dehydro-Pro | D-Ala | Trp |

In vitro and/or in vivo testing of the peptides specified in Table II shows that the peptides listed in Table II are considered effective to block GnRH-induced LH secretion in vitro at a reasonable concentration. Many of these peptides are more potent in vivo than the present standard. All of the peptides are considered to be effective to prevent ovulation of female mammals at very low dosages.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be higher. Overall, treatment of subjects with these peptides is generally carried out in the same manner as the clinical treatment using other antagonists of GnRH.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation- or chemo-therapy. Effective dosages will vary with the form of administration and the particular species of mammal being treated. An example of one typical dosage form is a bacteriostatic water solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. The substitutions in the phenyl ring of the Phe$^2$ residue may also be in the 3-position and in the 2,4 positions, which are considered equivalents. AAL ($\beta$-amino-Ala), aBu($\alpha,\gamma$ diamino butyric acid) or Orn can be substituted for Ser in the 4-position. L-Phe or L-Tyr having specific modifications present in the phenyl ring may be substituted in the 5-position; single substitutions for hydrogen should appear in either the 2- or 3-position, with the substitutions being chloro, fluoro, iodo, bromo or nitro, with chloro and fluoro being preferred. Instead of having either D-Ala-NH$_2$ or Gly-NH$_2$ at the C-terminus, Pro$^9$ can be linked to one of the following moieties which are considered to generally be equivalents thereof: Gly-OCH$_3$, Gly-OCH$_2$CH$_3$, Sar-NH$_2$, or NH-Y, with Y being lower alkyl, particularly ethyl, cycloalkyl, fluoro lower alkyl or

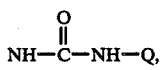

where Q is H or lower alkyl. Sar stands for sarcosine.

Particular features of the invention are emphasized in the claims which follow.

What is claimed is:

1. A peptide or a nontoxic salt thereof, said peptide having the formula: X-R$_1$-R$_2$-R$_3$-Ser-Tyr-R$_6$-R$_7$-Arg-Pro-R$_{10}$ wherein X is hydrogen or an acyl group having 7 or less carbon atoms; R$_1$ is 3,4 dehydro-Pro or $\beta$-D-NAL; R$_2$ is 4Cl-D-Phe, 4F-D-Phe, 4NO$_2$-D-Phe, C$^\alpha$Me4-Cl-D-Phe, 2,4Cl$_2$-D-Phe, 3,4Cl$_2$-D-Phe or 4Br-D-Phe; R$_3$ is (Y)D-Trp, with Y being N$^{in}$For or N$^{in}$Acetyl or a substitution in the 5- or 6-position selected from NO$_2$, NH$_2$, OCH$_3$, F, Cl, Br and CH$_3$; R$_6$ is D-Trp, D-Phe, D-Leu, D-Ile, D-Nle, D-Tyr, D-Val, D-Ala, D-Ser(OtBu), $\beta$-D-2NAL, (imBzl)D-His, 4-NH$_2$-D-Phe, D-Lys, D-Orn, D-Har, D-His, 4-gua-D-Phe, D-3PAL or D-Arg; R$_7$ is Phe, Tyr, Trp, 3PAL or 4F-D-Phe; and R$_{10}$ is Gly-NH$_2$ or D-Ala-NH$_2$; provided however that when R$_1$ is $\beta$-D-NAL, then R$_6$ is 4-NH$_2$-D-Phe, D-Lys, D-Orn, D-Har, D-His, 4-gua-D-Phe, D-3PAL or D-Arg.

2. A peptide in accordance with claim 1 wherein R$_2$ is 4Cl-D-Phe or 4F-D-Phe.

3. A peptide in accordance with claim 2 wherein R$_1$ is $\beta$-D-2NAL and R$_6$ is D-Arg.

4. A peptide in accordance with claim 3 wherein R$_3$ is (6NO$_2$) D-Trp.

5. A peptide in accordance with claim 4 wherein X is acetyl or acrylyl.

6. A peptide in accordance with claim 5 wherein R$_7$ is Tyr.

7. A peptide in accordance with claim 1 wherein X is Ac, R$_1$ is $\beta$-D-2NAL, R$_2$ is 4Cl-D-Phe, R$_6$ is D-Arg, R$_7$ is Tyr, and R$_{10}$ is D-Ala.

8. A peptide in accordance with claim 1 wherein R$_7$ is Tyr.

9. A peptide in accordance with claim 1 wherein R$_7$ is Phe.

10. A peptide in accordance with claim 1 wherein R$_7$ is Trp.

11. A peptide in accordance with claim 2 wherein R$_3$ is (N$^{in}$For) D-Trp, R$_7$ is Tyr and R$_{10}$ is Gly-NH$_2$.

12. A peptide in accordance with claim 2 wherein X is acetyl and R$_1$ is dehydro-Pro.

13. A peptide in accordance with claim 2 wherein R$_1$ is dehydro Pro, R$_3$ and R$_6$ are $\beta$-D-2NAL, and R$_7$ is Tyr.

14. A peptide or a nontoxic salt thereof, said peptide having the formula: X-$\beta$-D-NAL-R$_2$-R$_3$-Ser-Tyr-R$_6$-R$_7$-Arg-Pro-R$_{10}$ wherein X is hydrogen or an acyl group having 7 or less carbon atoms; R$_2$ is 4Cl-D-Phe, 4F-D-Phe, 4NO$_2$-D-Phe, C$^\alpha$-Me-4-Cl-D-Phe, 2,4Cl$_2$-D-Phe, 3,4Cl$_2$-D-Phe or 4Br-D-Phe; R$_3$ is D-Trp, (N$^{in}$-For)D-Trp, (6NO$_2$)D-Trp, $\beta$-D-NAL, or D-3PAL; R$_6$ is 4-NH$_2$-D-Phe, D-Lys, D-Orn, D-Har, D-His, 4-gua-D-Phe, D-3PAL, or D-Arg; R$_7$ is Phe, Tyr, Trp, 3PAL or 4F-D-Phe; and R$_{10}$ is Gly-NH$_2$ or D-Ala-NH$_2$.

15. A peptide in accordance with claim 14 having the formula acetyl-$\beta$-D-2NAL-4-Cl-D-Phe-D-Trp-Ser-Tyr-D-Arg-Tyr-Arg-Pro-D-Ala-NH$_2$.

16. A peptide in accordance with claim 14 wherein R$_7$ is Tyr.

17. A peptide in accordance with claim 14 wherein R$_7$ is Phe.

18. A peptide in accordance with claim 14 wherein R$_7$ is Trp.

19. A peptide in accordance with claim 14 wherein R$_7$ is 3PAL.

20. A pharmaceutical composition for inhibiting the secretion of gonadotropins in mammals comprising as an active ingredient an effective amount of a peptide as defined in claim 1 in association with a major amount of a nontoxic diluent.

21. A method for inhibiting the secretion of gonadotropins in mammals comprising administering an effective amount of a peptide or a nontoxic salt thereof, said peptide having the formula: X-R$_1$-R$_2$-R$_3$-Ser-Tyr-R$_6$-R$_7$-Arg-Pro-R$_{10}$ wherein X is hydrogen or an acyl group having 7 or less carbon atoms; R$_1$ is 3,4 dehydro-Pro or $\beta$-D-NAL; R$_2$ is 4Cl-D-Phe, 4F-D-Phe, 4NO$_2$-D-Phe, C$^\alpha$Me-4Cl-D-Phe, 2,4Cl$_2$-D-Phe, 3,4Cl$_2$-D-Phe or 4Br-D-Phe; R$_3$ is (Y)D-Trp, with Y being N$^{in}$For or N$^{in}$Acetyl or a substitution in the 5- or 6-position selected from NO$_2$, NH$_2$, OCH$_3$, F, Cl, Br and CH$_3$; R$_6$ is D-Trp, D-Phe, D-Leu, D-Ile, D-Nle, D-Tyr, D-Val, D-Ala, D-Ser(OtBu), $\beta$-D-2NAL, (imBzl)D-His, 4-NH$_2$-D-Phe, D-Lys, D-Orn, D-Har, D-His, 4-gua-D-Phe, D-3PAL or D-Arg; R$_7$ is Phe, Tyr, Trp, 3PAL or 4F-D-Phe; and R$_{10}$ is Gly-NH$_2$ or D-Ala-NH$_2$; provided however that when R$_1$ is $\beta$-D-NAL, then R$_6$ is 4-NH$_2$-D-Phe, D-Lys, D-Orn, D-Har, D-His, 4-gua-D-Phe, D-3PAL or D-Arg.

* * * * *

UNITED STATES PATENT AND TRADEMARK OFFICE
CERTIFICATE OF CORRECTION

PATENT NO. : 4,652,550

DATED : March 24, 1987

INVENTOR(S) : Jean E. F. Rivier, et al.

It is certified that error appears in the above-identified patent and that said Letters Patent is hereby corrected as shown below:

Column 5, line 41, Change "Cl-Phe" to --Cl-D-Phe--.

Column 6, line 14, After "trus" insert a comma (,).

Column 7, line 43, Change "$N^{\alpha}Boc-\alpha-D-2NAL$"

to --$N^{\alpha}Boc-\beta-D-2NAL$--.

Signed and Sealed this

Eighteenth Day of August, 1987

Attest:

DONALD J. QUIGG

Attesting Officer

Commissioner of Patents and Trademarks